(12) United States Patent
Zapf et al.

(10) Patent No.: US 7,633,026 B2
(45) Date of Patent: Dec. 15, 2009

(54) INDUCTIVE SWITCH

(75) Inventors: Martin Zapf, Creussen (DE); Thomas Luber, Hahnbach (DE)

(73) Assignee: ZF Friedrichshafen AG, Friedrchshafen (DE)

( * ) Notice: Subject to any disclaimer, the term of this patent is extended or adjusted under 35 U.S.C. 154(b) by 242 days.

(21) Appl. No.: 10/527,765

(22) PCT Filed: Sep. 11, 2003

(86) PCT No.: PCT/EP03/10126

§ 371 (c)(1),
(2), (4) Date: Apr. 6, 2005

(87) PCT Pub. No.: WO2004/027994

PCT Pub. Date: Apr. 1, 2004

(65) Prior Publication Data

US 2005/0258687 A1    Nov. 24, 2005

(30) Foreign Application Priority Data

Sep. 12, 2002 (DE) .................... 102 42 385

(51) Int. Cl.
*H03K 17/95* (2006.01)
(52) U.S. Cl. .................. 200/61.88; 324/207.15; 324/207.16; 324/207.18
(58) Field of Classification Search ............ 200/61.88, 200/61.91; 324/207.15–207.18; 331/65
See application file for complete search history.

(56) References Cited

U.S. PATENT DOCUMENTS

| | | | |
|---|---|---|---|
| 3,781,749 A | 12/1973 | Iles et al. | |
| 3,875,555 A | 4/1975 | Potter | |
| 4,580,478 A | 4/1986 | Brosh et al. | |
| 4,642,595 A | 2/1987 | Ruumpol | |
| 4,658,153 A | 4/1987 | Brosh et al. | |
| 4,843,259 A | 6/1989 | Weisshaupt | |
| 5,003,260 A | 3/1991 | Auchterlonie | |

(Continued)

FOREIGN PATENT DOCUMENTS

DE    26 53 371    9/1978

(Continued)

OTHER PUBLICATIONS

Apr. 1999 Radiation-proof proximity sensor, B.V. Jayawant et al., Measurement+Control 32 80-83.

*Primary Examiner*—Ramon M Barrera
(74) *Attorney, Agent, or Firm*—Jordan & Hamburg LLP (57) ABSTRACT

The invention relates to an inductive sensor unit having one or more sensor coils, which have been mounted on a printed circuit board in a planar manner. According to the invention, a change in the inductance of the sensor coils caused by leakage currents in the conductive actuator is correlated with the position of the actuator with regard to the distance from the sensor coil and with the overlapping of the sensor (at a fixed distance). This provides the basis for an inductive momentary contact switch and an inductive position switching device. The invention also relates to the evaluation of the inductance, e.g. of the momentary contact switch such as in inductive proximity switches by incorporating the inductive sensors in an oscillating circuit. Alternatively, the change in inductance can also be detected by a reactance measurement. A relative evaluation of the influence of adjacent sensor coils is carried out in position switching devices.

22 Claims, 6 Drawing Sheets

U.S. PATENT DOCUMENTS

| | | | |
|---|---|---|---|
| 5,079,523 | A | 1/1992 | Kleinhans |
| 5,233,294 | A | 8/1993 | Dreoni |
| 5,264,809 | A | 11/1993 | Tamino |
| 5,388,476 | A | 2/1995 | Harger et al. |
| 5,425,073 | A | 6/1995 | Bitzer et al. |
| 5,617,023 | A | 4/1997 | Skalski |
| 6,043,644 | A | 3/2000 | De Coulon et al. |
| 6,175,232 | B1 | 1/2001 | De Coulon et al. |
| 6,179,938 | B1 | 1/2001 | Mannhart et al. |
| 6,822,440 | B2 * | 11/2004 | Machul ................ 324/207.12 |
| 6,852,937 | B2 * | 2/2005 | Zapf et al. ............... 200/61.88 |
| 6,853,183 | B2 | 2/2005 | Kindler |
| 2008/0142346 | A1 | 6/2008 | Zapf et al. |
| 2008/0157756 | A1 | 7/2008 | Eissner et al. |

FOREIGN PATENT DOCUMENTS

| | | |
|---|---|---|
| DE | 85 11 731 | 6/1985 |
| DE | 3619238 | 3/1987 |
| DE | 3735694 | 5/1988 |
| DE | 3743259 | 6/1989 |
| DE | 40 38 515 | 6/1992 |
| DE | 198 06 529 | 8/1999 |
| DE | 101 25 278 | 12/2002 |
| EP | 0 447 653 | 9/1991 |
| EP | 0 455 613 | 11/1991 |
| EP | 0 537 747 | 4/1993 |
| EP | 0 805 339 | 11/1997 |
| EP | 0 936 385 | 8/1999 |
| FR | 28 03030 | 6/2001 |
| GB | 1415644 | 11/1975 |
| WO | WO- 02/01159 | 1/2002 |
| WO | WO- 2005/027347 | 3/2005 |

* cited by examiner

INDUCTIVE SWITCH

BACKGROUND OF THE INVENTION

The invention relates to an inductive sensor unit for switches and can be used in particular for a position switch apparatus that is used in automatic motor vehicle transmissions.

Known in the prior art is a displacement and angle sensor, in particular for determining a gear that has been selected in the motor vehicle field, in accordance with patent DE 198 06 529. The known displacement and angle sensor has four measurement coils that are arranged at right angles to one another on a coil carrier in an X/Y plane and are connected to evaluation electronics. The sensor has a so-called target that can be moved largely parallel to the X/Y plane relative to the measurement coils, thereby inducing voltages in the measurement coils. The evaluation electronics can determine the path traveled in the Y direction and the angle $\alpha$ of the target in a Z/X plane from the induced voltages. The known displacement and angle sensor is distinguished in that the opposing measurement coils are arranged spaced from one another and the adjacent measurement coils at least partially overlap one another.

The induction voltage is likewise used as a sensor signal in the older application in accordance with DE 101 25 278. The known designs have the disadvantage that a plurality of inductively acting sensor slides must be applied to the coil carrier, as is evident from the following background information.

Known in the field of automobiles is widespread employment of mechanical switches, including lock systems, operating elements for the dashboard, seat adjustments, mirror adjustments, etc. Mechanical switches have the disadvantage that they do not work in a wear-free manner. Their service life is limited by the material wear of the contact material, changes in the material (oxidation), and deposits on the switch contacts due to mechanical friction or electrical overloading or arcing when turning off.

One particular form of mechanical switches are mechanical sliding switches. A displaceable contact runs over a slide track and thus, depending on the position, produces a contact to various connections (so-called encoding switches). In such a shift gate unit, vibrations that occur in the vehicle lead to increased wear in the sliding contacts and slide tracks.

In modern vehicles, actuating motors these days are generally switched via wear-free power semiconductors, which then however are controlled by non-wear-free switches. In order to design the system completely wear-free, it is necessary to develop novel switches that work without mechanical switch contacts (that is, with sensors).

Known from the prior art are Hall sensors that react to the approach of permanent magnets and thus trigger a switching function. Furthermore, the use of GMR sensors, which are based on the effect of a change in resistance that is caused by an external magnetic field, is known. The external magnetic field can derive from a permanent magnet or a magnetizable plastic and can initiate appropriate switching functions.

Furthermore, the use of light cabinets and reflex light cabinets, which have the disadvantage that they are sensitive to stray light and that the optical components age and can be soiled easily, is known. The use of such sensors furthermore has the disadvantage that they are expensive compared to mechanical switches and inductive switches.

In switching elements, cost-effective printed circuit boards are frequently used as carriers for illumination, displays, or mechanical switches. The presence of such a printed circuit board favors the use of the present invention. The working principle of the inductive coupling of two sensor coils applied to the printed circuit board and their damping by a conductive actuator was disclosed as a cost-effective option in the older application in accordance with DE 101 25 278. In it, damping strength correlates to the position of the actuator relative to the sensors. In this technology, it can be disadvantageous that the sensors in their practical design must have a minimum size of approx. 10 mm×10 mm on the printed circuit board so that acceptable coupling can be achieved and thus the electronics can be designed simply and cost-effectively. In the printed circuit boards that can currently be economically produced, a local resolution of 0.12 mm is attained, i.e., the conductor width of the sensor windings can be a maximum of 0.12 mm, just like the insulating width between the windings. As a result of this, the transmitter coil and the receiver coil of the sensors can have only approx. 5 windings.

The object of the invention is to influence the inductance of a sensor coil using an actuator brought over the coil and to evaluate its inductance in a simple manner. The inductance of a coil changes significantly through a conductive actuator element that in accordance with the invention has a variable distance to the sensor coil and/or a variable overlap of the sensor coil. This object is attained by an inductive sensor unit in accordance with the invention.

SUMMARY OF THE INVENTION

An undamped sensor coil with the external dimensions 10 mm×10 mm, which is wound on the printed circuit board like a rectangular spiral from the inside to the outside, has 10 windings and an inductance of approx. 1 µH at the resolution that can be attained on the printed circuit board.

Although using the impedance of a spiral structure as a sensor is known from publication GB 1 415 644, the known spiral structure is double-wound in order to exploit the ohmic components of the spiral impedance and in order to switch off the inductive components of the spiral impedance. In contrast thereto, the sensor coil in accordance with the invention is single-wound, as can be seen from the following detailed description using the figures.

DETAILED DESCRIPTION OF THE INVENTION

Figure 1:
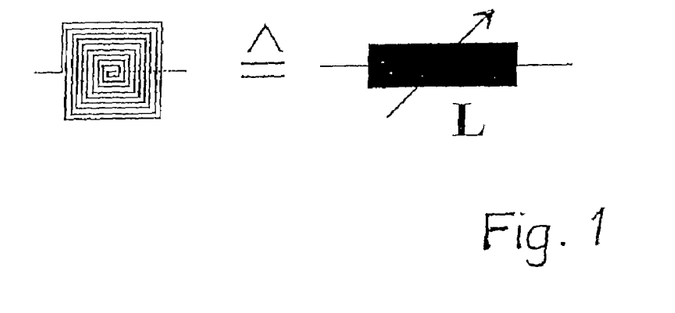
FIG. 1 illustrates the planar design of a sensor slide on a printed circuit board together with the electrotechnically equivalent symbol.
Figure 2:
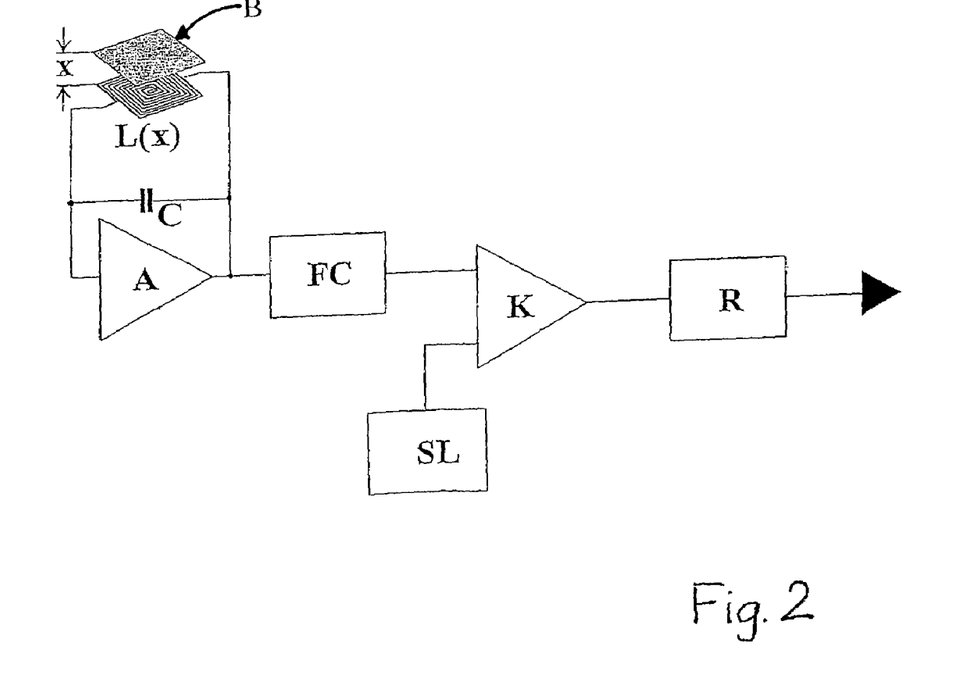
FIG. 2 illustrates a functional block diagram of an inventive sensor with an LC oscillating circuit as evaluation circuit.

In accordance with FIG. 1, a sensor coil is applied in a planar manner to a printed circuit board. The connection in the center point of the spiral is executed for instance on the back side of the printed circuit board. If the sensor is covered in accordance with FIG. 2 with a conductive actuator at a distance x of for instance x=0.05 mm, the inductance decreases from for instance approx. 1 µH to for instance approx. 0.2 µH.

The decrease in the induction using the actuator B is a function of the distance x from the actuator B to the sensor slide; however, it is also a function of the degree to which the sensor slide is covered by the actuator element. If the actuator covers the entire surface of the slide at a constant distance x, the amplitude of the sensor voltage is minimal with the degree of coverage of 100%, whereby the amount of the minimum sensor voltage depends on the distance x.

Figure 3:
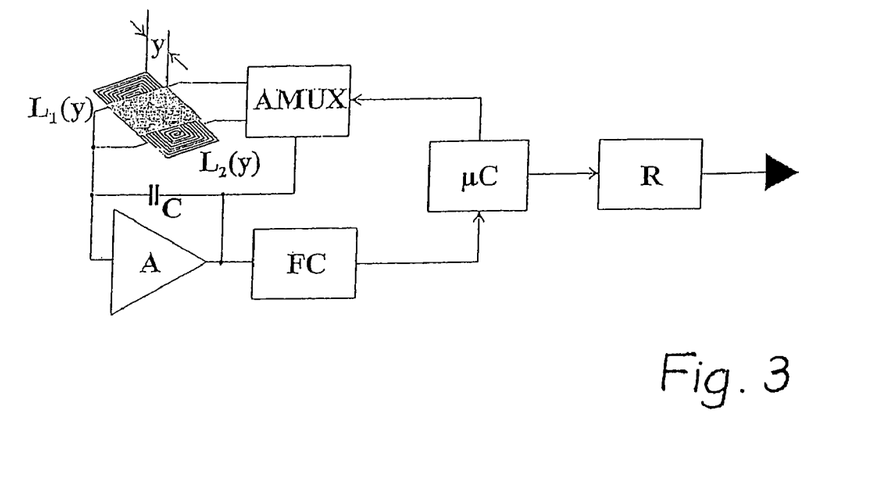
FIG. 3 illustrates a functional block diagram with an LC oscillating circuit and with two sensors for detecting a displacement path y.

Thus two switching mechanisms are possible for the switch:

The degree of coverage G is maintained at a defined size, and the distance x between the actuating element B and the sensor slide is varied (as illustrated e.g. in FIG. 2), or The distance x is maintained constant, and the degree of coverage G is changed (as illustrated e.g. in FIG. 3).

A combination of these two switch mechanisms is also possible.

Sufficiently known as cost-effective evaluation electronics is an LC oscillating circuit, comprising a sensor inductance L, a fixed capacitance C, and an inverting amplifier A into the feedback branch of which the LC oscillating circuit is built. Such a circuit is illustrated in a block diagram in FIG. 2. The frequency of the oscillating circuit is determined by the resonance frequency of the LC member using the formula:

$$f_r = \frac{1}{2\pi} \times \frac{1}{\sqrt{LC}}$$

In accordance with FIG. 3, a downstream frequency counter FC determines the oscillations per unit of time and outputs them as a signal value. For a simple switching function it is sufficient to compare the actual frequency value to a threshold value by means of a comparator and thus to initiate the switch function. In a normal case, the switch signal is set to "1" when the frequency is higher than a set limit frequency, which corresponds to a lower inductance through higher damping. At a lower frequency, the comparator outputs a "0". High powers can then be switched via a downstream high/low switch or a relay R. However, the functions of the frequency counter and comparator can also be realized as so-called firmware in a microcontroller.

Thus a wear-free momentary-contact switch can be realized in a simple manner in an operating unit of the automobile. In accordance with FIG. 2, the damping element is approached by depressing a key to the sensor and is held there by means of a locking mechanism. The lock is not released until the key is depressed again, and the actuator is brought to its rest position at a greater distance from the sensor (ballpoint pen locking principle). Thus keys such as the switches for hazard warning lights, fog lights, rear window defrost, etc., can be realized in a simple and cost-effective manner.

In applications in which very precise switching points are required, the effects of temperature on amplifiers, capacitors, comparators, etc., are often problematic. In temperature-stable applications, these effects can be circumvented in that two sensors are applied next to one another on one circuit board and they are alternately switched into the oscillating circuit (see FIG. 3). Switching on the inductance L1 or L2 occurs using a switching transistor or field effect transistor or MOSFET or an AMUX analog multiplexer. If a relative evaluation is applied in that the frequency ratio of the first sensor frequency to the second sensor frequency is used as switching criterion, the interfering effects are eliminated. The circuit is very temperature stable.

This type of circuit has also proved to be advantageous in applications in which the position y of the actuator is detected relative to the sensor positions, while the distance x from the actuator to the sensor is kept more or less constant (such as e.g. in displacement and angle sensors). In this case, as well, a relative evaluation takes place that can best occur, but must not exclusively occur, using a microcontroller µC.

Figure 4:
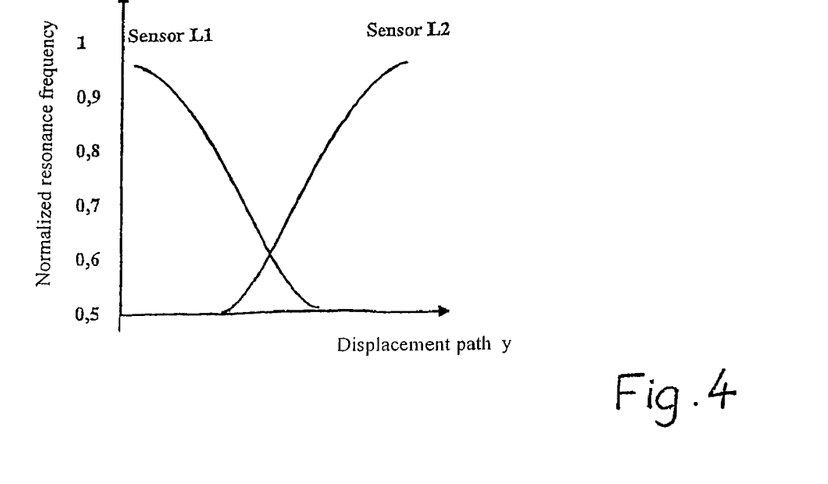
FIG. 4 illustrates a typical characteristic curve for the oscillating frequency with a first sensor L1 in accordance with FIG. 3 and a second sensor L2 in accordance with FIG. 3 as a function of the displacement path y.

FIG. 4 illustrates two typical characteristic curves of the normalized resonance frequency as a function of the displacement path y. The microcontroller µC can undertake precise position recognition in the displacement region between the peaks of the characteristic curves L1 and L2. In additional practical applications, even more sensors are used for recognizing the actuator position.

Figure 5:
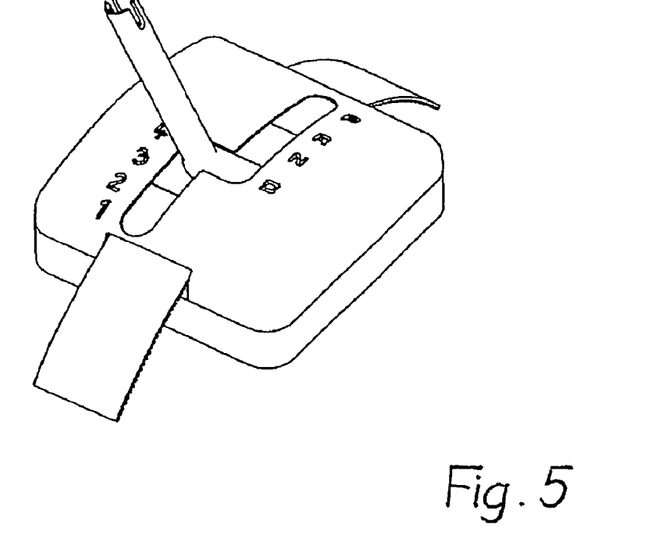
FIG. 5 illustrates a shift gate for a motor vehicle with an automatic gearshift lever that is connected to a sensor unit in accordance with FIG. 3.

If multiple positions are to be detected in one application event, such as is illustrated in FIG. 5 as a shift gate for a motor vehicle, it is useful to combine a plurality of inductive sensors as a functional unit. Given the example of converting the position recognition of an automatic gearshift lever, this looks as follows:

A printed circuit board is positioned under the cover as in FIG. 5; on its upper side e.g. the backlighting for the cover displays 1, 2, . . . P can be mounted. Connected to the automatic gearshift lever AW (see FIG. 6), which drops through a break in the printed circuit board, is an actuator slide BS that rests in a planar manner on the bottom side of the printed circuit board LP and to which are affixed one actuator or a plurality of actuators (e.g. the actuator surfaces BF1 and BF2 in FIG. 6). The actuator surfaces are pushed over the various sensor units SE at a defined distance.

The term displacement means a movement of the actuator slide that can be a straight line or that can change direction. The sensor coils to be passed over can be lined up in a straight line, as is shown in principle in FIG. 7. However, the sensor coils can also be situated adjacent to one another in accordance with a more complex topology, as is used for the shift gate units in accordance with FIGS. 6 and 9.

Figure 6:
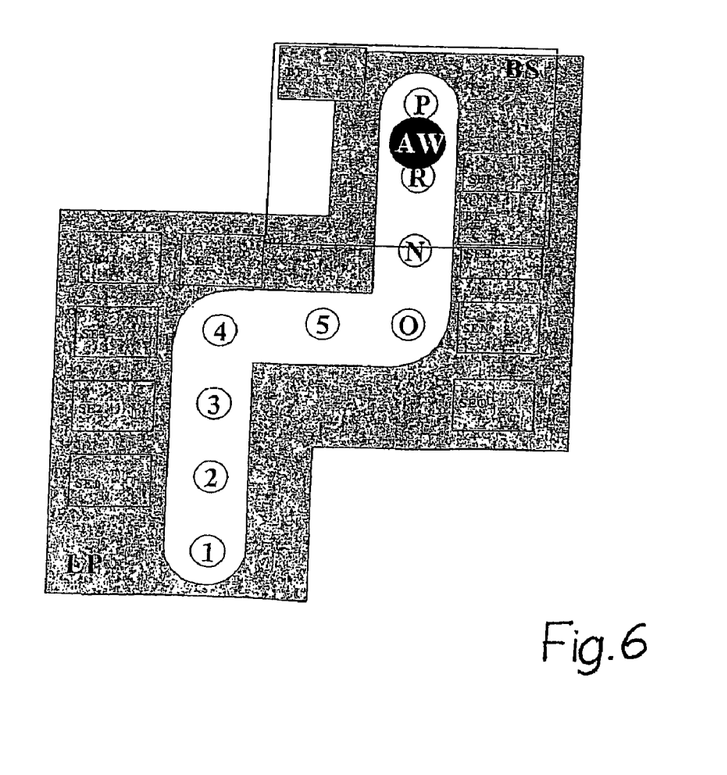
FIG. 6 illustrates the scheme of a printed circuit board with a plurality of sensor units for the shift gate unit in accordance with FIG. 5.
Figure 7:
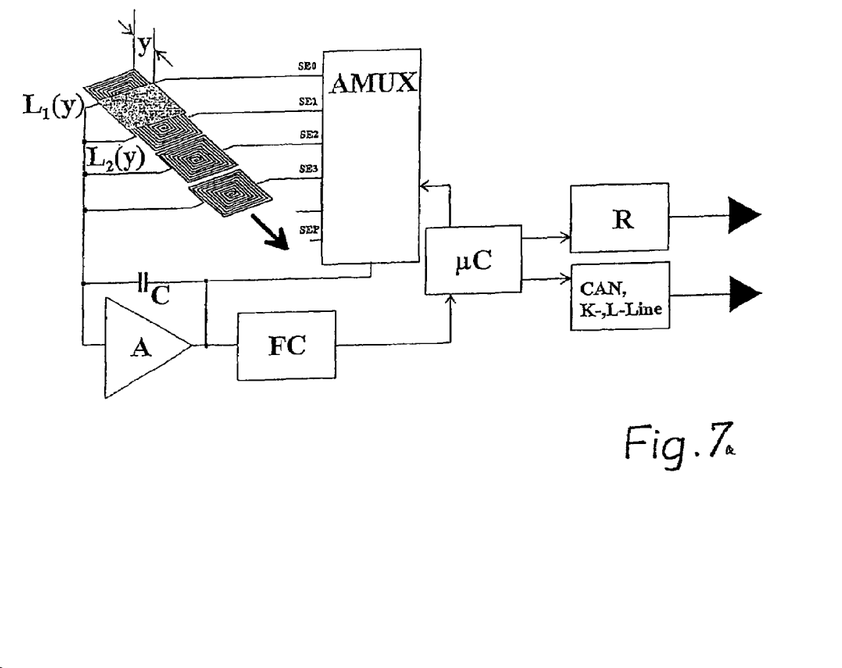
FIG. 7 illustrates the block diagram of an electronic unit when a plurality of inductive sensors are combined.

Furthermore, the topology of the adjacent sensor coils (straight line, polygon, other path) can be situated on a flat or on a curved printed circuit board. FIG. 7 depicts a flat arrangement of sensor coils, while FIGS. 5 and 6 depict an example for a curved printed circuit board that is arranged beneath the curved shift gate. In both cases the actuator slide is displaced at a distance that is largely constant above the arrangement of sensor coils.

Another variant of the claimed displacement results when the curved printed circuit board that follows the curved gate in accordance with FIG. 5 is replaced with a flat printed circuit board that is arranged in a plane that runs perpendicular to the surface of the gate. In this case the actuator slide is also positioned vertically and pushed sequentially over the sensor slides that are attached e.g. in arc-shapes to the vertical, flat printed circuit board.

Figure 8:
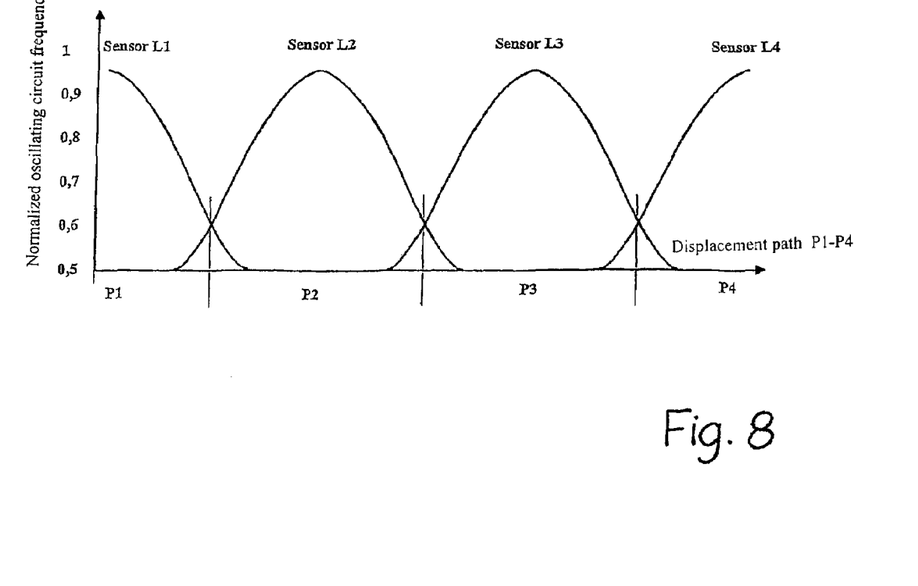
FIG. 8 illustrates the oscillating circuit frequency of the sensor signals of the different switch units in FIG. 7 during shifting events of the automatic gearshift lever from position 1 to position 4.

In the combination of a plurality of inductive switches, the block diagram looks like that in FIG. 7. The associated amplitudes of the sensor signals when the automatic gearshift lever is shifted can be seen in FIG. 8 for the positions 1, 2, 3, and 4, whereby the normalized oscillation frequency is applied across the displacement path P1-P4 for the sensors L1-L4. The shifting thresholds P1-P2, P2-P3, and P3-P4 are entered.

Figure 9:
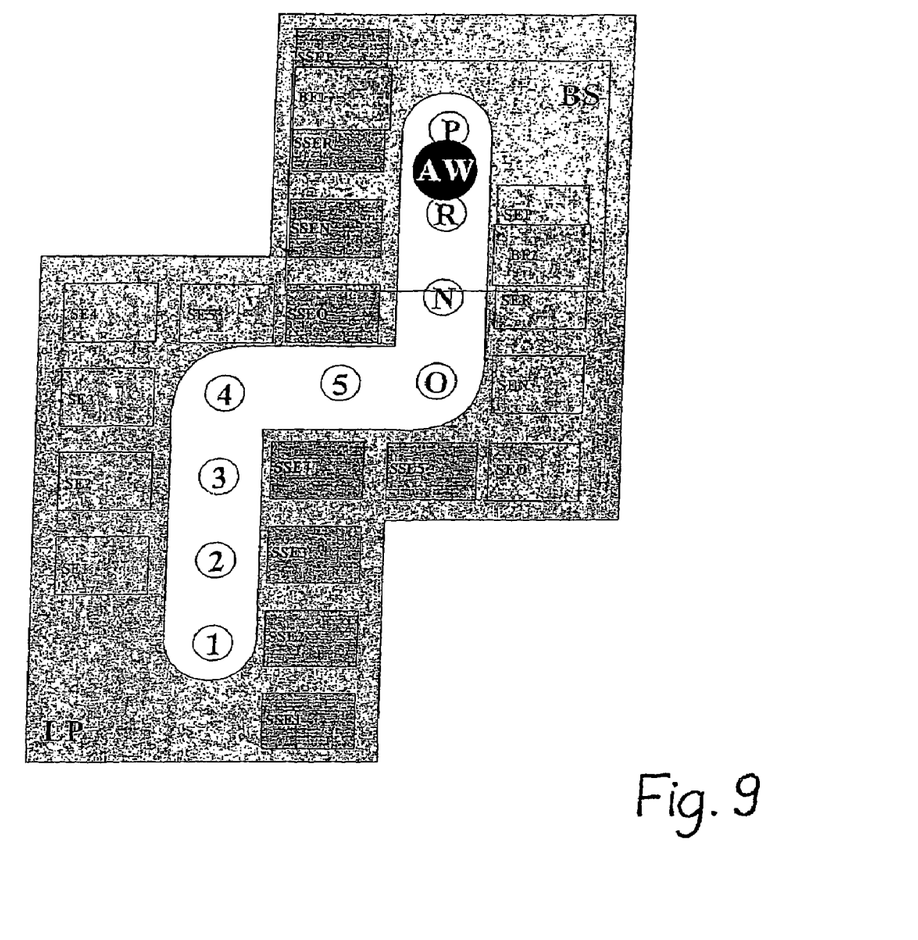
FIG. 9 illustrates a similar scheme of a printed circuit board as in FIG. 6, but with a redundant shifting unit.

Very redundant and therefore certain position recognition can also be realized without major additional complexity as depicted e.g. in FIG. 9. Instead of one sensor unit per position, it is suggested to construct two sensor units per position and to compare the signals. When there are contradictory results, the evaluation unit will perform the switching function so that the entire system is brought into a secure condition. For this, the printed circuit board can be expanded for instance with safety sensor units SSE in accordance with FIG. 9.

The evaluation unit for the sensor module will as a rule be a microcontroller that forwards the switching information to the control electronics or power electronics via an interface (CAN, LIN, etc.).

Figure 10:
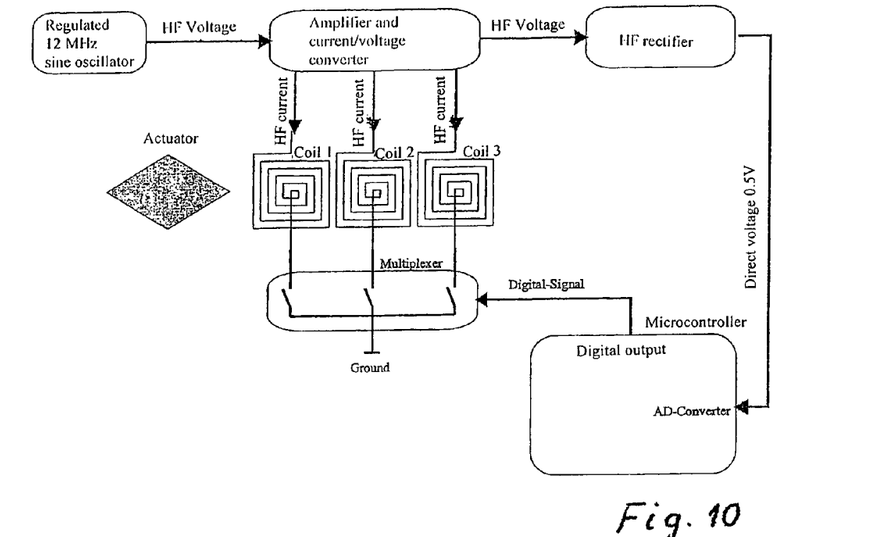
FIG. 10 illustrates the block diagram of an alternative evaluation unit.
Figure 11:
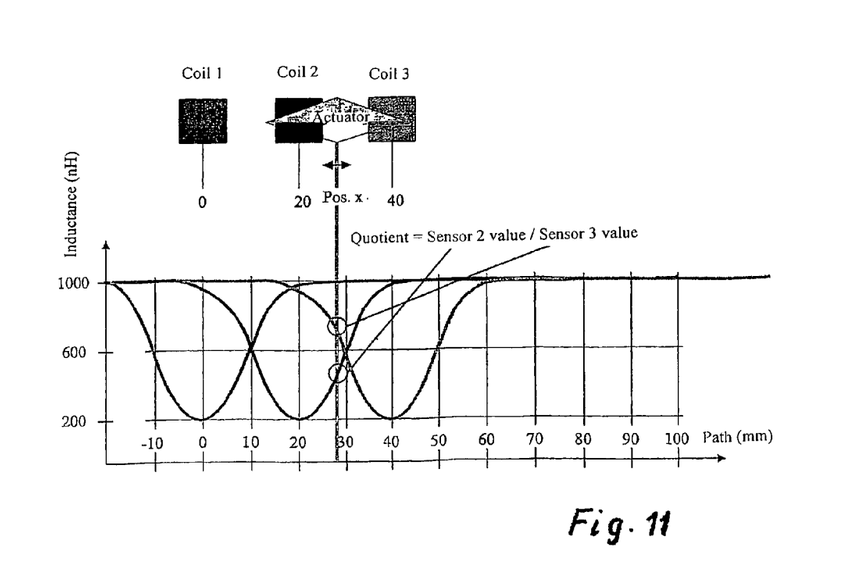
FIG. 11 illustrates the change in inductance evaluated in accordance with FIG. 10.

Signal evaluation occurs for a plurality of sensor coils via a multiplexer that switches on only one of the sensor coils of the evaluation circuit. FIGS. 10 and 11 illustrate another exemplary embodiment of the signal evaluation that can be employed alternative to the exemplary embodiment depicted in FIGS. 7 and 8.

In accordance with FIGS. 10 and 11, the limit between the positions of two adjacent sensor coils is determined by a direct comparison of the inductive reactance. In accordance with the block diagram in FIG. 10, a sine oscillator generates an alternating voltage of 12 MHz; this is amplified and fed as voltage into one of the three sensor coils that are switched into the time-division multiplex. If the actuator, which comprises conductive metal, is moved over the coils, the inductance of the coils decreases due to eddy current loss. Because of this, the reactance also decreases; it is calculated as follows: $XL=2*PI*f*L$ (f=12 MHz). If, for example, a coil has inductance of 1000 nH without actuator and 200 nH with actuator, the equation above results in XL of 75 Ohms and 15 Ohms, respectively. At constant alternating voltage, a current flows that depends on covering the actuator. This current is transformed into a proportional HF voltage and is fed equalized to the microcontroller.

FIG. 11 depicts the evaluation for the microcontroller. The microcontroller measures the voltage of each sensor cyclically in fixed time slits of e.g. 2 ms. If the actuator is moved in fixed path increments over the sensors and the voltages are recorded, the result is curves like those illustrated in FIG. 11. The path region can be enlarged with additional sensors. When the actuator is in the static condition, only 2 values are evaluated, i.e. there are only two adjacent measurement values for the microcontroller at any point in time. The quotient of two adjacent sensor voltages are calculated in the evaluation firmware in the microcontroller and compared to a fixed value. One or the other switch position is determined depending on whether the quotient is larger or smaller than the fixed value.

The invention claimed is:

1. An inductive momentary-contact switch comprising:
    a locking mechanism;
    a sensor unit including a printed circuit board having a sensor coil disposed thereon, and a conductive actuator element supported by said locking mechanism and displaceable relative to said sensor coil, and said sensor coil having a self-inductance which is predominantly determined by a distance between said conductive actuator and said sensor coil wherein a change in said distance produces a self-inductance change;
    an evaluation circuit configured to produce an oscillating signal in said sensor such that said sensor coil is conductively connected to said evaluation circuit and conductively driven with said oscillating signal by said evaluation circuit and the self-inductance change in said sensor coil initiates a switching function in said evaluation circuit based on changes in said oscillation signal caused by the self-inductance change.

2. The inductive momentary-contact switch in accordance with claim 1, wherein an alternating voltage of constant amplitude and constant frequency is injected into said sensor coil with subsequent evaluation of current amplitudes of the oscillation signal caused by said self-inductance change.

3. An inductive position switch apparatus comprising:
    a gearshift lever;
    an actuator slide;
    a sensor unit including a printed circuit board having at least first and second sensor coils disposed thereon adjacent each other in a common plane, and a conductive actuator element slidably supported by said actuator slide and movable by said gearshift lever, and disposed displaceable relative to said first and second sensor coils, and said first and second sensor coils respectively having first and second self-inductances which are predominantly determined by first and second relative positionings of said conductive actuator relative to a respective one of said first and second sensor coils wherein a change in said first and second relative positionings produces respectively first and second self-inductance changes in respective ones of said first and second sensor coils;
    an evaluation circuit configured to produce first and second oscillation signals in said first and second sensor coils, said first and second sensor coils being conductively connected to said evaluation circuit and conductively respectively driven with said first and oscillating signals by said evaluation circuit, and said evaluation circuit being configured to detect first and second signal changes in said first and second oscillation signals produced by said first and second self-inductance changes, and initiate a switching function based on a combination of said first and second signal changes; and
    the conductive actuator element being configured to simultaneously partially cover said first and second sensor coils and be movable relative to said first and second sensor coils to vary coverage such that a movement of said conductive actuator element produces said first and second signal changes as changes of a signal characteristic, and said first signal change is a change in said characteristic in an opposing direction of increase and decrease in comparison to changes of said characteristic in said second signal change based on a same movement of said conductive actuator.

4. The inductive position switch apparatus in accordance with claim 3 further comprising a multiplexer for selectively coupling said first and second sensor coils with the evaluation circuit for detection of said first and second oscillation signals.

5. The inductive position switch apparatus in accordance with claim 4 wherein only one of said first and second sensor coils is switched at any one time into said evaluation circuit and successive evaluations of said characteristic of said first and second signals are compared with each other in order to form a temperature-stable and precise switching criterion.

6. The inductive position switch apparatus in accordance with claim 5 further comprising an LC oscillating circuit, wherein said LC oscillating circuit successively applied to said first and second sensor coils.

7. The inductive position switch apparatus in accordance with claim 6 adapted for evaluating a resonance frequency of the LC oscillating circuit as said characteristic of said first and second signals.

8. The inductive position switch apparatus according to claim 4, wherein said characteristic is frequency.

9. The inductive position switch apparatus according to claim 4, further comprising an LC oscillating circuit, wherein said LC oscillating circuit is successively applied to said first and second sensor coils.

10. The inductive position switch apparatus in accordance with claim 3, wherein an alternating voltage of constant amplitude and constant frequency is injected into said first and second sensor coils with subsequent evaluation of current amplitudes of said first and second signals caused by the first and second self-inductance changes.

11. The inductive position switch apparatus according to claim 3, wherein said characteristic is frequency.

12. The inductive position switch apparatus according to claim 3, further comprising an LC oscillating circuit, wherein said LC oscillating circuit is successively applied to said first and second sensor coils.

13. An inductive switching apparatus comprising:
a positioning device including at least one of a locking mechanism or a gearshift lever;
a sensor unit including a printed circuit board having at least first and second sensor coils disposed thereon adjacent each other in a common plane, and a conductive actuator element movably supported by said positioning device, and disposed displaceable relative to said first and second sensor coils, and said first and second sensor coils respectively having first and second self-inductances which are predominantly determined by first and second relative positionings of said conductive actuator relative to a respective one of said first and second sensor coils wherein a change in said first and second relative positionings produces respectively first and second self-inductance changes in respective ones of said first and second sensor coils; and
an evaluation circuit configured to produce first and second oscillation signals in said first and second sensor coils, said first and second sensor coils being conductively connected to said evaluation circuit and conductively respectively driven with said first and oscillating signals by said evaluation circuit and said evaluation circuit being configured to detect first and second signal changes in said first and second oscillation signals produced by said first and second self-inductance changes, and initiate a switching function based on at least one of said first and second signal changes;
said switching function being based on at least one of:
a first switching function basis including said first and second relative positionings being effected by said locking mechanism setting first and second distances between said conductive actuator element to one of said first and second sensor coils along a direction normal to a plane of said first and second sensor coils; or
a second switching function basis including said first and second relative positionings being effected by said gear shift lever moving the conductive actuator element and the conductive actuator element being configured to simultaneously partially cover said first and second sensor coils and be movable relative to said first and second sensor coils by said gear shift lever to vary coverage which is overlapping of said first and second coils in said normal direction to said plane of said first and second coils such that a movement of said conductive actuator element produces said first and second signal changes as changes of a signal characteristic, and said first signal change is a change in said characteristic in an opposing direction of increase and decrease in comparison to changes of said characteristic in said second signal change based on a same movement of said conductive actuator.

14. The inductive switching apparatus in accordance with claim 13 further comprising an actuator slide, the coverage of said first and second sensor coils occurring by displacement of said actuator slide in a direction parallel to said plane of said first and second coils.

15. The inductive switching apparatus in accordance with claim 14, wherein only one of said first and second sensor coils is switched at any one time into said evaluation circuit and successive evaluations of said characteristic of said first and second signals are compared with each other in order to form a temperature-stable and precise switching criterion.

16. The inductive switching apparatus in accordance wilt claim 14 further comprising a multiplexer for selectively coupling said first and second sensor coils with the evaluation circuit for detection of said first and second oscillation signals.

17. The inductive switching apparatus in accordance with claim 15 further comprising a multiplexer for selectively coupling said first and second sensor coils with the evaluation circuit for detection of said first and second oscillation signals.

18. The inductive switching apparatus in accordance with claim 13 wherein only one of said first and second sensor coils is switched at any one time into said evaluation circuit and successive evaluations of said characteristic of said first and second signals are compared with each other in order to form a temperature-stable and precise switching criterion.

19. The inductive switching apparatus in accordance with claim 18 further comprising a multiplexer for selectively coupling said first and second sensor coils with the evaluation circuit for detection of said first and second oscillation signals.

20. The inductive switching apparatus in accordance with claim 13 further comprising a multiplexer for selectively coupling said first and second sensor coils with the evaluation circuit for detection of said first and second oscillation signals.

21. The inductive switch apparatus in accordance with claim 13, wherein an alternating voltage of constant amplitude and constant frequency is injected into said first and second sensor coils with subsequent evaluation of current amplitudes of said first and second signals caused by the first and second self-inductance changes.

22. The switching apparatus of claim 13 wherein:
said positioning device includes both said locking mechanism and said gearshift lever; and
said switching function includes first and second modes of operation respectively based on said first and second switching function bases.

* * * * *